United States Patent
Field et al.

(10) Patent No.: US 10,639,002 B2
(45) Date of Patent: May 5, 2020

(54) MEDICAL DEVICES

(71) Applicant: The Cooper Companies Global Holdings LP, St. Michael (BB)

(72) Inventors: Stephen James Field, Kent (GB); Richard Hingley, Kent (GB); Stephen James Lodge, Essex (GB); Thomas Cuthbert Mills, Kent (GB)

(73) Assignee: The Cooper Companies GLobal Holdings LP, St. Michael (BB)

( * ) Notice: Subject to any disclaimer, the term of this patent is extended or adjusted under 35 U.S.C. 154(b) by 0 days.

(21) Appl. No.: 13/914,684

(22) Filed: Jun. 11, 2013

(65) Prior Publication Data

US 2013/0281835 A1 Oct. 24, 2013

Related U.S. Application Data

(63) Continuation of application No. 10/803,882, filed on Mar. 19, 2004, now Pat. No. 10,045,756.

(30) Foreign Application Priority Data

Mar. 29, 2003 (GB) .................................... 0307350.9

(51) Int. Cl.
*A61B 8/08* (2006.01)
*A61M 25/00* (2006.01)
(Continued)

(52) U.S. Cl.
CPC .......... *A61B 8/0841* (2013.01); *A61B 8/0833* (2013.01); *A61L 29/18* (2013.01);
(Continued)

(58) Field of Classification Search
CPC ..... A61B 8/0841; A61B 8/481; A61B 8/0833; A61B 17/435; A61M 25/001; A61L 29/18
(Continued)

(56) References Cited

U.S. PATENT DOCUMENTS 2,702,034 A 2/1955 Walter
2,740,192 A 4/1956 Ogle
(Continued)

FOREIGN PATENT DOCUMENTS

DE 38 33 365 4/1989 .......... A61M 25/098
DE 39 36 162 6/1991 ............. A61B 17/22
(Continued)

OTHER PUBLICATIONS

Demand for Invalidation Trial to the Commissioner of the Japan Patent Office re Appeal Case for Invalidating JP Patent No. 4724372 dated Jan. 28, 2019.
(Continued)

*Primary Examiner* — Jeffrey G Hoekstra
*Assistant Examiner* — Patrick M Mehl
(74) *Attorney, Agent, or Firm* — Fish & Richardson P.C.

(57) ABSTRACT

An embryo transfer catheter or other medical device has a shaft extruded with two layers. The outer layer is relatively thick and contains gas bubbles sufficient to increase the visibility of the catheter under ultrasound observation but with a density that allows material within the catheter to be viewed by the eye. The inner layer is relatively thin and is free of bubbles so that it provides a smooth bore to the catheter.

17 Claims, 1 Drawing Sheet

(51) Int. Cl.
*A61B 17/435* (2006.01)
*A61L 29/18* (2006.01)
*A61B 90/00* (2016.01)

(52) U.S. Cl.
CPC ......... *A61M 25/001* (2013.01); *A61B 17/435* (2013.01); *A61B 2090/3925* (2016.02)

(58) Field of Classification Search
USPC .................................................. 600/458, 424
See application file for complete search history.

(56) References Cited

U.S. PATENT DOCUMENTS

| | | | |
|---|---|---|---|
| 2,989,053 A | 6/1961 | Hamilton | |
| 3,093,134 A | 6/1963 | Roehr | |
| 3,605,750 A | 9/1971 | Sheridan et al. | |
| 3,720,210 A | 3/1973 | Diettrich | |
| 4,265,251 A | 5/1981 | Tickner | |
| 4,386,628 A | 6/1983 | Stanley | |
| 4,582,061 A | 4/1986 | Fry | |
| 4,644,977 A | 2/1987 | Arterburn | |
| 4,701,161 A | 10/1987 | Lenck | |
| 4,731,052 A | 3/1988 | Seitz, Jr. | |
| 4,805,628 A | 2/1989 | Fry et al. | |
| 4,809,860 A | 3/1989 | Allen | |
| 4,810,244 A | 3/1989 | Allen | |
| 4,824,434 A | 4/1989 | Seitz, Jr. | |
| 4,832,681 A | 5/1989 | Lenck | |
| 4,869,259 A | 9/1989 | Elkins | |
| 4,874,649 A | 10/1989 | Daubenbüchel et al. | |
| 4,877,033 A | 10/1989 | Seitz, Jr. | |
| 4,877,615 A | 12/1989 | Taylor | |
| 5,048,530 A | 9/1991 | Hurwitz | |
| 5,071,425 A | 12/1991 | Gifford, III et al. | |
| 5,081,997 A | 1/1992 | Bosley, Jr. et al. | |
| 5,090,414 A | 2/1992 | Takano | |
| 5,149,328 A | 9/1992 | Zaha | |
| 5,160,319 A | 11/1992 | Emery et al. | |
| 5,195,979 A | 3/1993 | Schinkel et al. | |
| 5,201,314 A | 4/1993 | Bosley et al. | |
| 5,211,627 A | 5/1993 | William | |
| 5,250,649 A | 10/1993 | Onwumere et al. | |
| 5,259,837 A | 11/1993 | Van Wormer | |
| 5,273,527 A | 12/1993 | Schatz et al. | |
| 5,289,831 A | 3/1994 | Bosley | |
| 5,327,891 A * | 7/1994 | Rammler | A61B 8/0833 600/435 |
| 5,342,309 A | 8/1994 | Hausser | |
| 5,360,389 A | 11/1994 | Chenette | |
| 5,383,466 A | 1/1995 | Partika | |
| 5,405,321 A | 4/1995 | Reeves | |
| 5,415,634 A | 5/1995 | Glynn et al. | |
| 5,468,221 A * | 11/1995 | Schoner | A61L 29/18 138/137 |
| 5,596,990 A | 1/1997 | Yock et al. | |
| 5,611,345 A | 3/1997 | Hibbeln | |
| 5,622,665 A * | 4/1997 | Wang | 264/150 |
| 5,646,194 A | 7/1997 | Kobayashi et al. | |
| 5,688,490 A | 11/1997 | Tournier et al. | |
| 5,724,977 A | 3/1998 | Yock et al. | |
| 5,741,522 A | 4/1998 | Violante et al. | |
| 5,744,092 A | 4/1998 | Halgren et al. | |
| 5,759,154 A | 6/1998 | Hoyns | |
| 5,766,135 A | 6/1998 | Terwilliger | |
| 5,769,795 A | 6/1998 | Terwilliger | |
| 5,772,642 A | 6/1998 | Ciamacco, Jr. et al. | |
| 5,820,554 A | 10/1998 | Davis et al. | |
| 5,820,850 A | 10/1998 | Hashimoto et al. | |
| 5,827,174 A | 10/1998 | Reuss, Jr. et al. | |
| 5,843,023 A | 12/1998 | Cecchi | |
| 5,851,464 A * | 12/1998 | Davila et al. | 264/103 |
| 5,851,477 A | 12/1998 | Halgren et al. | |
| 5,879,305 A | 3/1999 | Yock et al. | |
| 5,921,933 A * | 7/1999 | Sarkis | A61B 8/0833 600/459 |
| 5,932,154 A | 8/1999 | Csongor et al. | |
| 5,932,299 A * | 8/1999 | Katoot | 427/508 |
| 5,939,015 A | 8/1999 | Csongor | |
| 5,945,061 A | 8/1999 | Csongor et al. | |
| 5,967,988 A | 10/1999 | Briscoe et al. | |
| 5,976,501 A | 11/1999 | Jablonski | |
| 6,010,448 A | 1/2000 | Thompson | |
| 6,018,676 A | 1/2000 | Davis et al. | |
| 6,024,727 A | 2/2000 | Thorne et al. | |
| 6,027,443 A | 2/2000 | Nag | |
| 6,030,369 A * | 2/2000 | Engelson | A61M 25/0045 604/264 |
| 6,063,221 A * | 5/2000 | Weinberg et al. | 156/203 |
| 6,071,580 A | 6/2000 | Bland et al. | |
| 6,074,578 A | 6/2000 | Csongor et al. | |
| 6,086,540 A | 7/2000 | Bonneville et al. | |
| 6,106,473 A | 8/2000 | Violante et al. | |
| 6,110,444 A | 8/2000 | Klaveness et al. | |
| 6,165,165 A * | 12/2000 | Cecchi | A61M 25/0009 264/209.1 |
| 6,207,752 B1 | 3/2001 | Abraham et al. | |
| 6,210,330 B1 | 4/2001 | Tepper | |
| 6,240,960 B1 | 6/2001 | Fillmore | |
| 6,261,241 B1 | 7/2001 | Burbank et al. | |
| 6,277,084 B1 | 8/2001 | Abele et al. | |
| 6,283,951 B1 | 9/2001 | Flaherty et al. | |
| 6,290,672 B1 | 9/2001 | Abae | |
| 6,306,094 B1 | 10/2001 | Joseph | |
| 6,312,429 B1 | 11/2001 | Burbank et al. | |
| 6,331,166 B1 | 12/2001 | Burbank et al. | |
| 6,344,026 B1 | 2/2002 | Burbank et al. | |
| 6,346,086 B1 | 2/2002 | Maksem et al. | |
| 6,347,241 B2 | 2/2002 | Burbank et al. | |
| 6,356,782 B1 | 3/2002 | Sirimanne et al. | |
| 6,358,211 B1 | 3/2002 | Mamayek | |
| 6,364,855 B1 | 4/2002 | Zappala | |
| 6,371,904 B1 | 4/2002 | Sirimanne et al. | |
| 6,371,973 B1 | 4/2002 | Tepper | |
| 6,427,081 B1 | 7/2002 | Burbank et al. | |
| 6,432,352 B1 | 8/2002 | Csongor | |
| 6,435,189 B1 | 8/2002 | Lewis et al. | |
| 6,454,727 B1 | 9/2002 | Burbank et al. | |
| 6,461,302 B1 | 10/2002 | Thompson | |
| 6,471,700 B1 | 10/2002 | Burbank et al. | |
| 6,481,462 B2 | 11/2002 | Fillmore et al. | |
| 6,497,706 B1 | 12/2002 | Burbank et al. | |
| 6,506,156 B1 | 1/2003 | Jones et al. | |
| 6,517,498 B1 | 2/2003 | Burbank et al. | |
| 6,527,752 B1 | 3/2003 | Bosley, Jr. et al. | |
| 6,540,693 B2 | 4/2003 | Burbank et al. | |
| 6,540,695 B1 | 4/2003 | Burbank et al. | |
| 6,544,185 B2 | 4/2003 | Montegrande | |
| 6,544,230 B1 | 4/2003 | Flaherty et al. | |
| 6,567,689 B2 | 5/2003 | Burbank et al. | |
| 6,508,773 B2 | 6/2003 | Burbank et al. | |
| 6,577,904 B1 | 6/2003 | Zhang et al. | |
| 6,610,005 B1 | 8/2003 | Tao | |
| 6,610,016 B1 | 8/2003 | Violante et al. | |
| 6,638,234 B2 | 10/2003 | Burbank et al. | |
| 6,656,407 B1 | 12/2003 | Halgren et al. | |
| 6,659,105 B2 | 12/2003 | Burbank et al. | |
| 6,662,041 B2 | 12/2003 | Burbank et al. | |
| 6,673,440 B2 | 1/2004 | Douglas et al. | |
| 6,676,658 B2 | 1/2004 | Burbank et al. | |
| 6,679,824 B1 | 1/2004 | Reed et al. | |
| 6,679,851 B2 | 1/2004 | Burbank et al. | |
| 6,685,648 B2 | 2/2004 | Flaherty et al. | |
| 6,689,071 B2 | 2/2004 | Burbank et al. | |
| 6,695,767 B2 | 2/2004 | Martinez Garcia et al. | |
| 6,695,787 B2 | 2/2004 | Hogendijk et al. | |
| 6,699,206 B2 | 3/2004 | Burbank et al. | |
| 6,712,775 B2 | 3/2004 | Burbank et al. | |
| 6,716,179 B2 | 4/2004 | Burbank et al. | |
| 6,723,052 B2 | 4/2004 | Mills | |
| 6,725,083 B1 | 4/2004 | Burbank et al. | |
| 6,736,409 B2 | 5/2004 | Hollenberg | |
| 6,749,554 B1 | 6/2004 | Snow et al. | |
| 6,758,848 B2 | 7/2004 | Burbank et al. | |
| 6,761,680 B2 | 7/2004 | Terwilliger et al. | |

(56) References Cited

U.S. PATENT DOCUMENTS

| | | |
|---|---|---|
| 6,786,858 B2 | 9/2004 | Terwilliger et al. |
| 6,838,278 B2 | 1/2005 | Fortino |
| 6,840,090 B2 | 1/2005 | Smith |
| 6,860,856 B2 | 3/2005 | Ward et al. |
| 6,862,470 B2 | 3/2005 | Burbank et al. |
| 6,875,168 B2 | 4/2005 | Bateman et al. |
| 6,875,182 B2 | 4/2005 | Wardle et al. |
| 6,905,458 B2 | 6/2005 | Choay et al. |
| 6,958,044 B2 | 10/2005 | Burbank et al. |
| 6,993,375 B2 | 1/2006 | Burbank et al. |
| 6,996,433 B2 | 2/2006 | Burbank et al. |
| 6,997,885 B2 | 2/2006 | Lubock et al. |
| 7,014,610 B2 | 3/2006 | Koulik |
| 7,047,063 B2 | 5/2006 | Burbank et al. |
| 7,060,020 B2 | 6/2006 | Terwilliger et al. |
| 7,188,537 B2 | 3/2007 | Junger |
| 7,189,206 B2 | 3/2007 | Quick et al. |
| 7,229,413 B2 | 6/2007 | Violante et al. |
| 7,229,418 B2 | 6/2007 | Burbank et al. |
| 7,229,439 B2 | 6/2007 | Burbank et al. |
| 7,235,052 B2 | 6/2007 | Kellar et al. |
| 7,258,669 B2 | 8/2007 | Russell |
| 7,261,712 B2 | 8/2007 | Burbank et al. |
| 7,264,596 B2 | 9/2007 | Burbank et al. |
| 7,282,034 B2 | 10/2007 | Burbank et al. |
| 7,322,938 B2 | 1/2008 | Burbank et al. |
| 7,322,939 B2 | 1/2008 | Burbank et al. |
| 7,322,940 B2 | 1/2008 | Burbank et al. |
| 7,329,228 B2 | 2/2008 | Burbank et al. |
| 7,357,794 B2 | 4/2008 | Makower et al. |
| 7,357,801 B2 | 4/2008 | Burbank et al. |
| 7,377,902 B2 | 5/2008 | Burbank et al. |
| 7,382,857 B2 | 6/2008 | Engel |
| 7,384,391 B2 | 6/2008 | Spittle et al. |
| 7,470,249 B2 | 12/2008 | Junger |
| 7,488,295 B2 | 2/2009 | Burbank et al. |
| 7,565,191 B2 | 7/2009 | Burbank et al. |
| 7,625,347 B2 | 12/2009 | Burbank et al. |
| 7,637,904 B2 | 12/2009 | Wingler et al. |
| 7,651,467 B2 | 1/2010 | Lubock et al. |
| 7,651,505 B2 | 1/2010 | Lubock et al. |
| 7,668,582 B2 | 2/2010 | Sirimanne et al. |
| 7,736,337 B2 | 6/2010 | Diep et al. |
| 7,792,569 B2 | 9/2010 | Burbank et al. |
| 7,794,402 B2 | 9/2010 | Wang |
| 7,819,819 B2 | 10/2010 | Quick et al. |
| 7,867,169 B2 | 1/2011 | Webler et al. |
| 7,879,011 B2 | 2/2011 | Chang |
| 7,887,737 B2 | 2/2011 | Mejlhede et al. |
| 7,970,454 B2 | 6/2011 | Jones et al. |
| 7,983,734 B2 | 7/2011 | Jones et al. |
| 8,052,669 B2 | 11/2011 | Lee-Sepsick et al. |
| 8,092,390 B2 | 1/2012 | Field |
| 8,137,346 B2 | 3/2012 | Burbank et al. |
| 8,147,487 B2 | 4/2012 | Burbank et al. |
| 8,152,737 B2 | 4/2012 | Burbank et al. |
| 8,177,792 B2 | 5/2012 | Lubock et al. |
| 8,200,313 B1 | 6/2012 | Rambod et al. |
| 8,219,182 B2 | 7/2012 | Burbank et al. |
| 8,224,424 B2 | 7/2012 | Burbank et al. |
| 8,229,553 B2 | 7/2012 | Burbank et al. |
| 8,273,009 B2 | 9/2012 | Arabia et al. |
| 8,282,573 B2 | 10/2012 | Shabaz et al. |
| 8,303,509 B2 | 11/2012 | Webler et al. |
| 8,306,602 B2 | 11/2012 | Sirimanne et al. |
| 8,320,993 B2 | 11/2012 | Sirimanne et al. |
| 8,320,994 B2 | 11/2012 | Sirimanne et al. |
| 8,343,071 B2 | 1/2013 | Shabaz et al. |
| 8,360,990 B2 | 1/2013 | Shabaz et al. |
| 8,361,082 B2 | 1/2013 | Jones et al. |
| 8,377,109 B2 | 2/2013 | Vrba et al. |
| 8,382,674 B2 | 2/2013 | Webler |
| 8,398,596 B2 | 3/2013 | Field |
| 8,430,863 B2 | 4/2013 | Webler |
| 8,460,204 B2 | 6/2013 | Quick et al. |
| 8,465,412 B2 | 6/2013 | Kamrava |
| 8,498,693 B2 | 7/2013 | Jones et al. |
| 8,560,052 B2 | 10/2013 | Mills |
| 8,585,596 B1 | 11/2013 | Flaherty et al. |
| 8,600,481 B2 | 12/2013 | Sirimanne et al. |
| 8,603,121 B2 | 12/2013 | Surti et al. |
| 8,622,887 B2 | 1/2014 | Gergeley |
| 8,626,269 B2 | 1/2014 | Jones et al. |
| 8,626,270 B2 | 1/2014 | Burbank et al. |
| 8,633,023 B2 | 1/2014 | Du et al. |
| 8,636,734 B2 | 1/2014 | Burbank et al. |
| 8,656,928 B2 | 2/2014 | Carlson et al. |
| 8,663,116 B2 | 3/2014 | Hamilton, Jr. |
| 8,672,892 B2 | 3/2014 | Carr et al. |
| 8,690,752 B2 | 4/2014 | Jose |
| 8,718,745 B2 | 5/2014 | Burbank et al. |
| 8,784,433 B2 | 7/2014 | Lubock et al. |
| 8,795,452 B2 | 8/2014 | Alpert et al. |
| 8,834,370 B2 | 9/2014 | Evert et al. |
| 8,880,154 B2 | 11/2014 | Jones et al. |
| 8,936,553 B2 | 1/2015 | Stigall et al. |
| 8,951,195 B2 | 2/2015 | Sheldon et al. |
| 8,959,753 B2 | 2/2015 | Garbini et al. |
| 8,965,486 B2 | 2/2015 | Burbank et al. |
| 9,033,889 B2 | 5/2015 | Hamilton, Jr. |
| 9,034,363 B2 | 5/2015 | Doshi et al. |
| 9,044,162 B2 | 6/2015 | Jones et al. |
| 9,044,215 B2 | 6/2015 | Shabaz et al. |
| 9,085,097 B2 | 7/2015 | Lentz et al. |
| 9,107,640 B2 | 8/2015 | Ho et al. |
| 9,149,341 B2 | 10/2015 | Jones et al. |
| 9,179,935 B2 | 11/2015 | Zarnescu et al. |
| 9,204,866 B2 | 12/2015 | Shabaz et al. |
| 9,216,012 B2 | 12/2015 | Burbank et al. |
| 9,216,037 B2 | 12/2015 | Buster et al. |
| 9,220,880 B2 | 12/2015 | Lee-Sepsick et al. |
| 9,237,937 B2 | 1/2016 | Burbank et al. |
| 9,242,076 B2 | 1/2016 | Burton et al. |
| 9,247,960 B2 | 2/2016 | Carson et al. |
| 9,320,540 B2 | 4/2016 | Badie |
| 9,636,082 B2 | 5/2017 | Field |
| 9,642,591 B2 | 5/2017 | Field et al. |
| 2002/0026117 A1 | 2/2002 | Joseph |
| 2002/0134850 A1 | 9/2002 | Hollenberg |
| 2002/0177776 A1 | 11/2002 | Crawford Keller et al. |
| 2003/0032896 A1* | 2/2003 | Bosley, Jr. ............ A61B 17/435 600/585 |
| 2003/0040756 A1* | 2/2003 | Field .......................... 606/108 |
| 2003/0050531 A1 | 3/2003 | Field |
| 2003/0206864 A1 | 11/2003 | Mangin |
| 2003/0208101 A1 | 11/2003 | Cecchi |
| 2004/0230119 A1 | 11/2004 | Brustad et al. ............... 600/442 |
| 2005/0074406 A1 | 4/2005 | Couvillon, Jr. et al. |
| 2005/0143656 A1 | 6/2005 | Burbank et al. |
| 2006/0089608 A1 | 4/2006 | Shaykh et al. |
| 2006/0095015 A1 | 5/2006 | Hobbs et al. |
| 2006/0106338 A1 | 5/2006 | Chang |
| 2007/0167822 A1 | 7/2007 | Webler et al. |
| 2007/0179575 A1 | 8/2007 | Esch et al. |
| 2007/0255140 A1 | 11/2007 | Violante et al. |
| 2007/0265516 A1 | 11/2007 | Wang |
| 2008/0058702 A1 | 3/2008 | Arndt et al. |
| 2008/0154136 A1 | 6/2008 | Webler |
| 2010/0256577 A1 | 10/2010 | Field |
| 2010/0331955 A1 | 12/2010 | Vrba et al. |
| 2013/0281835 A1 | 10/2013 | Field et al. |

FOREIGN PATENT DOCUMENTS

| | | | |
|---|---|---|---|
| DE | 40 14 998 | 11/1991 | ............ A61M 25/01 |
| DE | 299 08 256 | 7/1999 | ............ A61B 8/14 |
| DE | 197 27 740 | 9/1999 | ............ A61B 8/12 |
| EP | 0 033 659 | 8/1981 | ............ A61M 25/00 |
| EP | 0 072 671 | 2/1983 | ............ A61B 10/00 |
| EP | 0 083 973 | 7/1983 | ............ A61B 10/00 |
| EP | 0 109 657 | 5/1984 | ............ A61M 25/00 |
| EP | 0 131 166 | 1/1985 | ............ A61M 1/00 |
| EP | 0 243 341 | 10/1987 | ............ A61M 5/14 |
| EP | 0 323 527 | 7/1989 | ............ A61M 1/00 |

(56) References Cited

FOREIGN PATENT DOCUMENTS

| | | | |
|---|---|---|---|
| EP | 0 356 774 | 3/1990 | ............ A61M 25/00 |
| EP | 0 382 392 | 8/1990 | ............ A61B 19/00 |
| EP | 0 386 936 | 9/1990 | ............ A61B 8/08 |
| EP | 0 481 685 | 4/1992 | ............ A61B 19/00 |
| EP | 0 526 669 | 2/1993 | ............ A61M 25/00 |
| EP | 0 552 924 | 7/1993 | ............ A61B 8/08 |
| EP | 0 567 285 | 10/1993 | ............ A61M 25/00 |
| EP | 0 586 056 | 3/1994 | ............ A61B 17/425 |
| EP | 0 624 342 | 11/1994 | ............ A61B 8/08 |
| EP | 0 701 836 | 3/1996 | ............ A61M 25/01 |
| EP | 0 935 442 | 8/1999 | ............ A61B 8/00 |
| EP | 0 941 128 | 9/1999 | ............ A61K 49/00 |
| EP | 0 995 459 | 4/2000 | ............ A61M 25/00 |
| EP | 0 996 363 | 5/2000 | ............ A61B 8/00 |
| EP | 1 105 170 | 6/2001 | ............ A61L 31/00 |
| EP | 1 109 496 | 6/2001 | ............ A61B 10/00 |
| EP | 1 132 049 | 9/2001 | ............ A61B 8/08 |
| EP | 1 139 878 | 10/2001 | ............ A61B 17/00 |
| EP | 1 146 910 | 10/2001 | ............ A61K 49/00 |
| EP | 1 152 696 | 11/2001 | ............ A61B 17/00 |
| EP | 1 155 418 | 11/2001 | ............ G21G 4/08 |
| EP | 1 118 337 | 1/2002 | |
| EP | 1 166 720 | 1/2002 | ............ A61B 10/00 |
| EP | 1 173 096 | 1/2002 | ............ A61B 8/08 |
| EP | 1 177 776 | 2/2002 | ............ A61D 19/02 |
| EP | 1 189 546 | 3/2002 | ............ A61B 19/00 |
| EP | 1 196 107 | 4/2002 | ............ A61B 19/00 |
| EP | 1 274 353 | 1/2003 | ......... A61B 17/435 |
| EP | 1 358 856 | 11/2003 | ............ A61D 19/02 |
| EP | 1 450 891 | 9/2004 | ............ A61N 5/10 |
| EP | 0 941 128 | 10/2004 | ............ A61K 49/00 |
| EP | 1 491 147 | 12/2004 | ............ A61B 17/00 |
| EP | 1 494 721 | 1/2005 | ............ A61B 19/00 |
| EP | 1 513 581 | 3/2005 | ............ A61M 37/00 |
| EP | 1 525 856 | 4/2005 | ............ A61B 19/00 |
| EP | 1 599 125 | 11/2005 | ............ A61B 10/00 |
| EP | 1 626 667 | 2/2006 | ............ A61B 19/00 |
| EP | 1 667 589 | 6/2006 | ............ A61B 17/43 |
| EP | 1 696 800 | 9/2006 | ............ A61B 10/00 |
| EP | 1 781 178 | 5/2007 | ............ A61B 10/00 |
| EP | 1 919 388 | 5/2008 | ............ A61M 37/00 |
| EP | 1 967 147 | 9/2008 | ............ A61B 17/34 |
| EP | 2 103 266 | 9/2009 | ............ A61B 17/435 |
| EP | 2 114 270 | 11/2009 | ............ A61B 17/435 |
| EP | 2 174 596 | 4/2010 | ............ A61B 17/00 |
| EP | 2 319 449 | 5/2011 | ............ A61B 90/00 |
| EP | 2 389 868 | 11/2011 | ............ A61B 10/00 |
| EP | 2 407 111 | 1/2012 | ............ A61B 10/02 |
| EP | 2 407 119 | 1/2012 | ............ A61B 19/00 |
| EP | 2 517 630 | 10/2012 | ............ A61B 8/12 |
| EP | 2 555 687 | 2/2013 | ............ A61B 10/02 |
| EP | 2 564 890 | 3/2013 | ............ A61M 25/10 |
| EP | 2 570 150 | 3/2013 | ............ A61M 25/10 |
| EP | 2 620 111 | 7/2013 | ............ A61B 17/34 |
| EP | 2 641 546 | 9/2013 | ............ A61B 10/02 |
| EP | 2 984 991 | 2/2016 | ............ A61B 10/02 |
| EP | 2 995 260 | 3/2016 | ............ A61B 10/02 |
| FR | 2 716 266 | 8/1995 | ............ G01S 15/02 |
| GB | 829383 | 3/1960 | |
| GB | 894653 | 4/1962 | |
| GB | 1.151222 | 5/1969 | ............ A61M 5/28 |
| GB | 2 263 642 | 8/1995 | ............ A61M 25/01 |
| GB | 2 274 991 | 10/1996 | |
| GB | 2 379 610 | 3/2003 | |
| GB | 2 381 198 | 4/2003 | ............ A61M 25/01 |
| GB | 2 388 784 | 11/2003 | ............ A61B 17/435 |
| GB | 2 380 944 | 10/2004 | ............ A61M 25/095 |
| GB | 2 379 610 | 1/2005 | ............ A61L 29/00 |
| GB | 2494395 | 1/2014 | ............ A61M 25/10 |
| GB | 2494864 | 2/2014 | ............ A61M 25/10 |
| GB | 2469839 | 9/2014 | ............ A61B 8/00 |
| JP | S 53-66986 | 6/1978 | ............ B32B 5/18 |
| JP | 55-125876 | 9/1980 | ............ A61M 25/00 |
| JP | 58-92951 | 6/1983 | ............ A61M 25/00 |
| JP | 58-198353 | 11/1983 | ............ A61M 25/00 |
| JP | 3-14451 | 2/1991 | ............ A61B 17/22 |
| JP | 06-327671 | 11/1994 | ............ A61B 8/00 |
| JP | 8-173543 | 7/1996 | ............ A61M 25/00 |
| JP | H 09-123302 | 5/1997 | ............ B29D 24/00 |
| JP | 2844238 | 1/1999 | ............ A61B 8/00 |
| JP | 2001-504101 | 3/2001 | ............ A61K 49/00 |
| JP | 2002-106759 | 4/2002 | ............ F16L 11/11 |
| JP | 2002-234066 | 8/2002 | ............ B29C 47/90 |
| JP | 2003-190275 | 7/2003 | ............ A61L 29/00 |
| SU | 1255450 | 9/1986 | ............ B29C 47/12 |
| WO | WO 94/17743 | 8/1994 | ............ A61B 17/435 |
| WO | WO 95/23615 | 9/1995 | ............ A61K 49/00 |
| WO | 98/19713 | 5/1998 | |
| WO | WO 99/03399 | 1/1999 | ............ A61B 8/00 |
| WO | 00/09178 | 2/2000 | |
| WO | WO 2001/13021 | 2/2001 | ............ F16L 11/04 |
| WO | WO 02/02171 | 1/2002 | ............ A61M 25/00 |

OTHER PUBLICATIONS

Coloreu, B. et al., "Embryo transfer under ultrasound guidance improves pregnancy rates after in-vitro fertilization", *Human Reproduction*, vol. 15, No. 3, pp. 616-620 (2000).

Hale, Lyndon, "Embryo transfer: how to ensure correct placement in utero", *Reproduction, Fertility and Development*, vol. 13, pp. 95-98 (2001).

Strickler, Ronald C. et al., "Ultrasound guidance for human embryo transfer", *Fertility and Sterility*, vol. 43, No. 1, pp. 54-61 (Jan. 1985).

Wood, Ellen G. et al., "Ultrasound-guided soft catheter embryo transfers will improve pregnancy rates in in-vitro fertilization", *Human Reproduction*, vol. 15, No. 1, pp. 107-112 (2000).

Woolcott, Robert et al., "Potentially important variables identified by transvaginal ultrasound-guided embryo transfer", *Human Reproduction*, vol. 12, No. 5, pp. 963-966 (1997).

\* cited by examiner

MEDICAL DEVICES

BACKGROUND OF THE INVENTION

This invention relates to medical devices.

The invention is more particularly concerned with catheters or the like, that are visible under ultrasound observation.

Ultrasound imaging equipment is increasingly being used during surgical procedures to monitor the location of a device within the body. The visibility of a device under ultrasound depends on various factors including the difference between the acoustic impedance of the material of the device and that of the surrounding medium, such as the patient tissue or body fluid w thin which the device is located. This difference is relatively low with plastic devices such as catheters and may make conventional catheters difficult to locate. Even devices of metal, such as needles, present problems of visibility under ultrasound observation because of the directional nature of the reflections. In some orientations a metal needle may be clearly visible but in other orientations it may be considerably less visible.

Attempts have been made to increase the visibility of medico-surgical devices under ultrasound observation in various ways. The surface of the device may be modified, such as by forming grooves or indentations in its surface. A reflective coating may be applied to the device, such as incorporating bubbles, as described in WO98/19713 and EP0624342. Alternatively, a metal marker may be secured to a plastics catheter. GB2379610 describes a catheter where the wall is made entirely of a plastics including gas bubbles or where bubble-containing material is in a stripe occupying only a part of the circumference. Although this latter form of catheter has various advantages, it has been found that there is a tendency for the surface of the bore through the catheter to be interrupted by small protrusions where the bubbles break the surface. In some applications, such as for embryo transfer, It is important that the bore of the catheter is as smooth as possible so any interruption of this is a disadvantage. In other applications it may be important instead for the outer surface to be as smooth as possible, or for both the outer and inner surface to be smooth.

BRIEF SUMMARY OF THE INVENTION

It is an object of the present invention to provide an alternative medical device.

According the present invention there is provided a medical device having an elongate portion of plastics material, the portion being extruded with at least a first, inner layer and a second layer on the outside of the inner layer one of the layers being substantially free of gas bubbles and the other of the layers including gas bubbles dispersed within it to increase the visibility of the device under ultrasound imaging.

The layer substantially free of gas bubbles may be thinner than the other layer. The layer substantially free of gas bubbles may be the inner layer. The second layer may provide an outer surface of the catheter. The device may include a third layer on the outside of the second layer. The second layer may contain gas bubbles and the first and third layers may be substantially free of gas bubbles. The bubbles may be in a region extending around the entire circumference of the device. The bubbles preferably extend in a continuous region along the length of the device. The gas bubbles may have a size in the range 0.1µ to 300µ, preferably having a size in the range 1µ to 50µ and roost preferably having a size in the range 5µ to 10µ. The gas bubbles may be provided by gas-filled polymer microspheres. The device may be a catheter having a bore extending along its length. The inner layer may have an inner surface providing the bore of the catheter. The plastics material is preferably transparent to the eye, the density of bubbles being such as to permit material within the catheter to be viewed by the eye.

An embryo-transfer catheter and its method of manufacture, according to the present invention, will now be described, by way of example, with reference to the accompanying drawing.

DETAILED DESCRIPTION OF THE PREFERRED EMBODIMENTS

Figure 1:
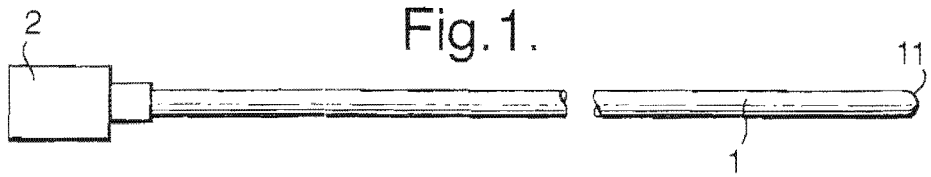
FIG. 1 is a side elevation view of the catheter.
Figure 2:
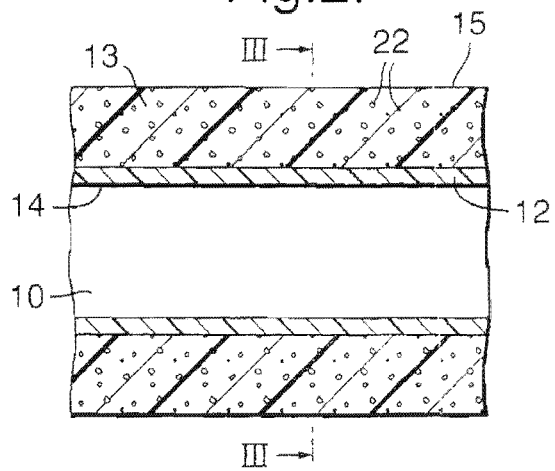
FIG. 2 is a sectional side elevation view of the catheter of FIG. 1 to a larger scale.
Figure 3:
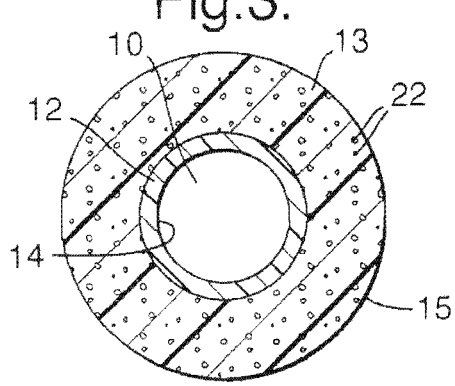
FIG. 3 is a cross-section view of the catheter along the line III-III of FIG. 2.

With reference first to FIGS. 1 to 3, the catheter comprises art elongate portion in the form of a flexible shaft 1 and a hub 2 joined at the rear end of the shaft. The shaft 1 has a circular section and a bore 10 extending along its length. The shaft 1 opens at its forward, right-hand, patient end 11, which is atraumatically rounded.

The shaft 1 is extruded in two layers 12 and 13. The first, inner layer 12 is of a clear, transparent polyurethane material and is free of gas bubbles so that its inner surface 14, providing the surface of the bore 10, is completely smooth. The second layer 13 is formed around the entire circumference of the first layer 12 and its outer surface 15 provides the outer surface of the catheter. The second layer 13 incorporates small, gas-filled bubbles 22 the size and distribution of which are selected to increase the visibility of the catheter under ultrasound observation. Typically, the gas bubbles have a diameter in the range of about 0.1µ to 300µ, preferably being between 1µ and 50µ with the most preferred range being about 5µ to 10µ. The bubbles 22 extend uniformly through the thickness and around the circumference of the second layer 13 and may be spherical or of any other regular or irregular shape. The second layer 13 is preferably made from the same plastics material as the first layer and the gas bubbles are preferably provided by incorporating gas-filled polymer microspheres such as of the kind sold under the trade mark Expancel ("Expancel" is a registered trade mark of Akzo Nobel). The bubble-filled layer 13 is preferably as thick as possible so as to increase the visibility of the catheter under ultrasound observation. The inner layer 12 may be relatively in since its purpose is solely to provide a smooth inner surface for the catheter.

The hub 2 serves to make connection with the shaft 1 and is moulded from a rigid, transparent plastics material, being subsequently bonded with the rear end of the shaft.

Figure 4:
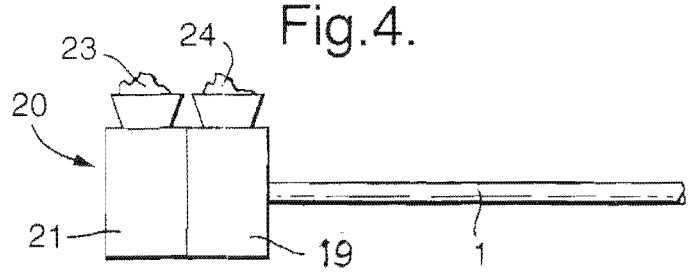
FIG. 4 illustrates schematically manufacture of the catheter.

The shaft 1 is extruded in the manner shown in FIG. 4 using an extrusion machine 20. The machine 20 has two extrusion heads 21 and 19, winch are supplied respectively with a polyurethane material 23 and with a polyurethane material 24 containing hollow microspheres. The two materials 23 and 24 are heated and supplied to the respective extrusion heads 21 and 19 so that tubing is formed with the bubble-filled material 24 coextruded as the outer layer 13 about the outside of the inner layer 12, which is of the bubble-free material 23. The shaft 1 can be extruded continuously at low cost, without the need for any subsequent operations apart from attaching the hub 2 and end forming the patient end tip 11.

The bubbles could be formed in various other ways, such as by injecting gas into the melt. Alternatively, chemical foaming agents could be added to the plastics material, such as: azocarbonomides, dinitrosopentmethelyene-tetramine, benzenephonohydrazine, 4,4 oxybis(benzenephonohydrazine), NN$^1$dimethyl-NN$^1$ dinitrosoterephthalamide, azoisobutyronitrile, sodium bicarbonate, terephthalazide or trihydrazinatrazine. Another way of forming the gas bubbles would be by incorporating a liquid into the plastics melt which volatises during the melt process. Alternatively, solid powdered dry ice (carbon dioxide) could be incorporated into the melt so that the particles of dry ice become gas bubbles during the forming process. It might be possible to use other solids which undergo sublimation in this way. The bubbles could be formed directly as a result of chemical reaction during polymerisation and or alternatively during cross-linking. The bubbles could be formed mechanically by whipping the plastics in a liquid form, such as in the manner used to form latex foam. Alternatively, small particles of a soluble material could be added to the plastics melt and subsequently dissolved away.

Figure 5:
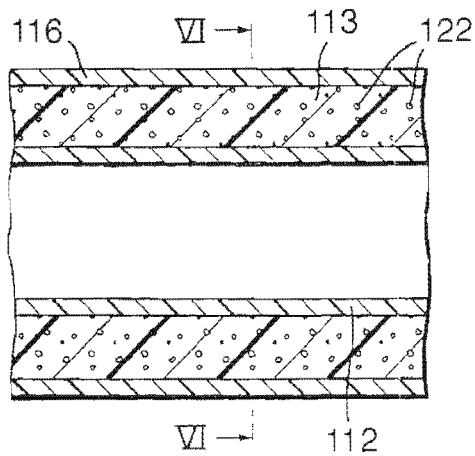
FIG. 5 is a sectional side elevation view of a part of an alternative catheter.
Figure 6:
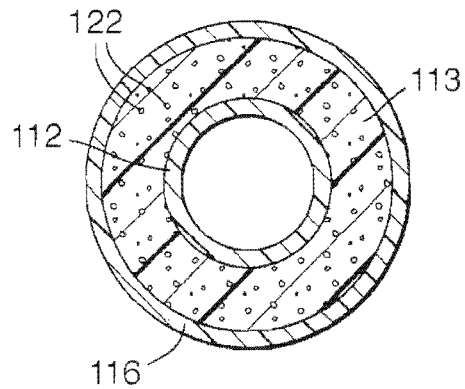
FIG. 6 is a cross-section view of the catheter of FIG. 5 along the line VI-VI.

The bubble-filled layer need not provide the outer surface of the catheter, especially where the outer surface of the catheter needs to be smoother than can be provided by a bubble layer with bubbles 122. Instead, as shown in FIGS. 5 and 6, the bubble-filled layer 113 could be sandwiched between an inner layer 112 and a third, outer layer 116, the inner and outer layers being of the same material and being free of bubbles. Preferably, the inner layer 112 and the outer layer 116 are relatively thin and the middle, bubble-filled layer 113 is relatively thick, to maximise the ultrasound reflecting properties of the catheter. This three-layer tube is also made by co-extruding the three layers with one another. Alternatively, where it was necessary for the outer surface of the catheter to be smooth and there was no need for the bore to be smooth, the catheter could just have two layers where the outer layer was thin and bubble-free and the inner layer was thicker and contained bubbles.

The catheter could have any number of additional layers with one or more layers containing bubbles.

Catheters according to the present invention can be made having good visibility under ultrasound imaging without producing multiple echoes. They can produce a good image regardless of the orientation of the catheter shaft. The shaft can be made sufficiently transparent to ultrasound energy to enable material flowing along the bore of the catheter to be observed on the ultrasound image.

Because the catheter does not require any coating or separate marker there is no need for subsequent assembly operations and there is no risk of detachment. The catheter can be made of conventional, medically-approved materials so does not present any new risk to the patient. The outer surface of the three-layer catheter can be smooth so the catheter can be inserted or slid through an outer tube with low friction. A smooth bore can be provided to a catheter to ensure free flow along the bore, which can be important where the catheter is used to transfer embryos. In other applications, a smooth inner surface may reduce the accumulation of biofilm in the catheter. The catheter can be made without the need for metal components, which can be an advantage where the catheter is used while the patient is being viewed by magnetic imaging techniques. The catheter can be completely transparent to x-rays or the plastics from which it is formed could incorporate an x-ray opaque filler, such as barium sulphate.

The bubble size and density can be selected so that the optical transparency of the plastics forming the shaft remains sufficient to enable material flowing along the shaft to be viewed by the eye.

It is not essential for the bubbles to be provided around the entire circumference of the bubble-containing layer, instead, the bubbles could just be provided along a longitudinal stripe in the layer. This arrangement can be used where the shaft needs to have increased clarity so that material within the catheter can be seen by the eye. Alternatively, the bubbles could be contained around the entire circumference of the layer apart from a bubble-free longitudinal strip. The bubble region need not be continuous along the length of the catheter. Instead, discrete separate regions with bubbles could be separated from one another along the length of the catheter by regions without bubbles. A shaft for such a catheter could be made by blowing gas into the plastics forming the bubble layer and by interrupting the gas flow. Where the bubbles are contained within a stripe, this could be interrupted to make it discontinuous by extruding the stripe using two auxiliary extruders, one having material with hollow microspheres and the other having material without the microspheres. Alternate extruders would be switched on and off so that the stripe could have sections containing bubbles separated from one another by sections without bubbles. A catheter having a layer with an interrupted bubble region may give a clearer ultrasound indication of movement of the catheter along its length and may also enable clearer observation of material flowing along the catheter both by ultrasound and by the eye.

The invention is not confined to catheters but could be used in other medical devices such as cables and medical devices without a bore, or with more than one bore.

What we claim is:

1. A surgical procedure comprising:
    placing a medical device within a patient, the medical device having an elongate portion of a first layer of a first polymeric material and a second layer of a second polymeric material formed around the first layer, the first and second layers being coextruded from the first and second polymeric materials, respectively, the second polymeric material being the same as the first polymeric material, the first layer being extruded to be substantially free of gas bubbles and forming an innermost layer of the elongate portion of the medical device, and the second layer being extruded to include gas bubbles dispersed in its polymeric material and forming an outermost layer of the elongate portion of the medical device, and the first layer that is substantially free of gas bubbles being thinner than the second layer that includes the gas bubbles such that the second layer forms a main substrate of the elongate portion of the medical device; and
    using ultrasound imaging equipment to monitor a location of the medical device within the patient, the location of the medical device within the patient being readily observable by the ultrasound equipment due to the second layer of the medical device that includes gas bubbles providing increased visibility of the medical device under ultrasound imaging.

2. The procedure of claim 1, wherein the elongate portion is a catheter having a bore defined by an inner wall of the first layer.

3. The procedure of claim 2, wherein the elongate portion is an embryo transfer catheter, and the first and second polymeric materials are sufficiently transparent to ultrasound energy to enable an embryo moving within a lumen of the catheter to be monitored by the ultrasound imaging equipment.

4. A method of manufacturing a medical device usable for ultrasound imaging, the method comprising the steps of:
supplying a first polymeric material to an extrusion machine;
supplying a second polymeric material to the extrusion machine, the second polymeric material being the same as the first polymeric material;
coextruding the first and second polymeric materials with one another to form an elongate tubing with a first layer of the first polymeric material forming an inner wall of the tubing to define a bore of the tubing and a second layer of the second polymeric material formed around the first layer to form an outermost surface of the tubing of the medical device;
wherein the first layer of polymeric material is substantially free of gas bubbles and the second layer of polymeric material includes gas bubbles dispersed within its polymeric material to increase the visibility of the medical device under ultrasound imaging; and
wherein the first layer that is substantially free of gas bubbles is thinner than the second layer that includes the gas bubbles such that the second layer forms a main substrate of the elongate tubing of the medical device.

5. The method of claim 4, further comprising the step of:
providing gas-filled polymer microspheres to the second polymeric material to form the gas bubbles, wherein the gas bubbles have a size in the range 0.1µ to 300µ.

6. The method of claim 4, wherein the coextruding step comprises extruding the second layer of the tubing to be thicker than the first layer.

7. The method of claim 4, wherein the medical device is a catheter and the elongate tubing of the catheter has first and second ends, the method further comprising the steps of:
adding a hub to one of the first and second ends of the catheter; and
rounding the other of the first and second ends to prevent trauma to the patient when the catheter is inserted into the patient.

8. A method of monitoring the location of a medical device within a patient, comprising:
placing within the patient a medical device having an elongate portion with a first layer of a first polymeric material and a second layer of a second polymeric material coextruded with one another so that second layer is formed around the first layer, the second polymeric material being the same as the first polymeric material, the first layer being substantially free of gas bubbles and forming an innermost layer of the elongate portion of the medical device, and the second layer including gas bubbles dispersed in its polymeric material to increase the visibility of the elongate portion under ultrasound imaging and forming an outermost layer of the elongate portion of the medical device, and the first layer that is substantially free of gas bubbles being thinner than the second layer that includes the gas bubbles such that the second layer forms a main substrate of the elongate portion of the medical device; and
using ultrasound imaging equipment to monitor the location of the medical device within the patient.

9. A method of manufacturing an embryo transfer catheter adapted to be viewed under ultrasound imaging, the method comprising:
supplying a first polymeric material to an extrusion machine;
supplying a second polymeric material to the extrusion machine, the second polymeric material being the same as the first polymeric material;
coextruding the first and second polymeric materials with one another to form an elongate tubing of the embryo transfer catheter, the elongate tubing consisting of a first layer of the first polymeric material forming an inner wall of the tubing to define a bore of the tubing and a second layer of the second polymeric material formed around the first layer and forming an outermost surface of the tubing of the embryo transfer catheter;
wherein the first layer is extruded to be substantially free of gas bubbles and the second layer is extruded to include gas bubbles dispersed in its polymeric material, wherein the first layer that is substantially free of gas bubbles is thinner than the second layer that includes the gas bubbles such that the second layer forms a main substrate of the embryo transfer catheter, and wherein the visibility of the embryo transfer catheter under ultrasound imaging is increased due to the gas bubbles dispersed in the polymeric material of the second layer.

10. The method of claim 9, further comprising the step of:
selecting a size and density of the gas bubbles so that the optical transparency of the polymeric materials is sufficiently transparent to enable an embryo moving within the bore of the elongate tubing to be viewed by eye.

11. The method of claim 10, further comprising the step of:
selecting the size of the gas bubbles to be in the range of 0.1µ to 300µ.

12. The method of claim 9, further comprising the step of:
selecting the size of the bubbles to be in the range of 1µ to 50µ.

13. The method of claim 9, wherein the coextruding step further comprises:
coextruding the first layer that is substantially free of gas bubbles to form a smooth surface for the inner wall that defines the bore of the elongate tubing to reduce trauma to embryos moving through the elongate tubing.

14. A method of manufacturing a medical device viewable under ultrasound imaging, the method comprising the steps of:
supplying a first polymeric material to an extrusion machine for extrusion as a first layer substantially free of gas bubbles;
supplying a second polymeric material to the extrusion machine for extrusion as a second layer including gas bubbles, the second polymeric material being the same as the first polymeric material;
coextruding the first and second polymeric materials with one another to form an elongate tubing consisting of the first and second layers, the first layer forming an inner wall of the elongate tubing to define a bore of the elongate tubing and the second layer formed around the first layer and forming an outermost surface of the elongate tubing of the medical device, wherein the first layer that is substantially free of gas bubbles is thinner than the second layer that includes the gas bubbles such that the second layer forms a main substrate of the elongate tubing of the medical device;

wherein visibility of the medical device under ultrasound imaging is increased due to the medical device having the second layer that includes gas bubbles, and wherein the first and second polymeric materials are sufficiently transparent to ultrasound energy to enable material moving within the bore of the elongate tubing to be visualized under ultrasound imaging.

15. The method of claim 14, further comprising the step of:

selecting a size of the bubbles to be in the range 0.1µ to 300µ.

16. The method of claim 14, further comprising the step of:

selecting a size of the bubbles to be in the range of 1µ to 50µ.

17. The method of claim 14, further comprising the step of:

selecting a size of the bubbles to be in the range of 5µ to 10µ.

\* \* \* \* \*

UNITED STATES PATENT AND TRADEMARK OFFICE
CERTIFICATE OF CORRECTION

PATENT NO. : 10,639,002 B2
APPLICATION NO. : 13/914684
DATED : May 5, 2020
INVENTOR(S) : Stephen James Field et al.

Page 1 of 1

It is certified that error appears in the above-identified patent and that said Letters Patent is hereby corrected as shown below:

On the Title Page

Column 1
Item (73) (Assignee), Line 1, delete "GLobal" and insert -- Global --

In the Claims

Column 5
Line 39, in Claim 5, after "range" insert -- of --

Column 7
Line 14, in Claim 15, after "range" insert -- of --

Signed and Sealed this
Thirtieth Day of June, 2020

Andrei Iancu
*Director of the United States Patent and Trademark Office*